United States Patent
Ichikawa et al.

(10) Patent No.: US 10,500,570 B2
(45) Date of Patent: Dec. 10, 2019

(54) FORMED BODY AND METHOD FOR PRODUCING THE SAME, α-OLEFIN DIMERIZATION CATALYST, AND METHOD FOR PRODUCING α-OLEFIN DIMER

(71) Applicant: MITSUI CHEMICALS, INC., Tokyo (JP)

(72) Inventors: Shinichiro Ichikawa, Chiba (JP); Naoya Takahashi, Nagareyama (JP); Masami Murakami, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 337 days.

(21) Appl. No.: 15/103,216

(22) PCT Filed: Dec. 10, 2014

(86) PCT No.: PCT/JP2014/082757
§ 371 (c)(1),
(2) Date: Jun. 9, 2016

(87) PCT Pub. No.: WO2015/093378
PCT Pub. Date: Jun. 25, 2015

(65) Prior Publication Data
US 2016/0296919 A1 Oct. 13, 2016

(30) Foreign Application Priority Data
Dec. 17, 2013 (JP) .................................. 2013-260226

(51) Int. Cl.
*B01J 27/232* (2006.01)
*B01J 37/04* (2006.01)
(Continued)

(52) U.S. Cl.
CPC ............. *B01J 27/232* (2013.01); *B01J 21/18* (2013.01); *B01J 23/04* (2013.01); *B01J 27/236* (2013.01);
(Continued)

(58) Field of Classification Search
None
See application file for complete search history.

(56) References Cited

U.S. PATENT DOCUMENTS

| 3,972,721 | A | * | 8/1976 | Hammel | B01D 67/0058 501/33 |
| 4,520,126 | A | | 5/1985 | Kawamoto | |
| 5,081,094 | A | * | 1/1992 | Drake | B01J 27/232 502/174 |

FOREIGN PATENT DOCUMENTS

| CN | 1178133 A | 4/1998 |
| GB | 2276833 A1 | 10/1994 |

(Continued)

OTHER PUBLICATIONS

Chinese Office Action dated Jun. 20, 2017 issued in the Chinese patent application No. 201480068134.5 and its partial English translation.
(Continued)

*Primary Examiner* — Philip Y Louie
*Assistant Examiner* — Ali Z Fadhel
(74) *Attorney, Agent, or Firm* — Rankin, Hill & Clark LLP

(57) ABSTRACT

Provided is a formed body containing at least one carbonate compound (A1) selected from $Na_2CO_3$ or $K_2CO_3$, the formed body having a volume of pores with a pore diameter of from 0.05 μm to 10 μm of from 0.10 mL/g to 0.30 mL/g and a crushing strength of from 1.8 kgf to 10.0 kgf.

12 Claims, 1 Drawing Sheet

(51) Int. Cl.
*C07C 2/14* (2006.01)
*B01J 37/02* (2006.01)
*B01J 23/04* (2006.01)
*B01J 27/236* (2006.01)
*B01J 35/10* (2006.01)
*B01J 21/18* (2006.01)
*B01J 35/00* (2006.01)
*B01J 37/08* (2006.01)
*C07C 2/24* (2006.01)
*B01J 35/12* (2006.01)

(52) U.S. Cl.
CPC ......... *B01J 35/002* (2013.01); *B01J 35/1038* (2013.01); *B01J 35/1066* (2013.01); *B01J 37/023* (2013.01); *B01J 37/04* (2013.01); *B01J 37/08* (2013.01); *C07C 2/14* (2013.01); *C07C 2/24* (2013.01); *B01J 35/1071* (2013.01); *B01J 35/1076* (2013.01); *B01J 35/12* (2013.01); *C07C 2521/18* (2013.01); *C07C 2523/04* (2013.01); *C07C 2527/232* (2013.01)

(56) References Cited

FOREIGN PATENT DOCUMENTS

| | | |
|---|---|---|
| JP | 58114737 A2 | 7/1983 |
| JP | 342043 | 2/1991 |
| JP | 7222927 A2 | 8/1995 |
| JP | 2006326418 A2 | 12/2006 |
| JP | 2008149275 A2 | 7/2008 |
| KR | 19870000972 | 5/1987 |

OTHER PUBLICATIONS

Extended European Search Report dated Jul. 27, 2017 issued in the European patent application No. 14871087.4.
Korean Office Action dated Jul. 28, 2017 issued in the Korean patent application No. 2016-7015747 and its partial English translation.
International Search Report dated Mar. 10, 2015 filed in PCT/JP2014/082757.

\* cited by examiner

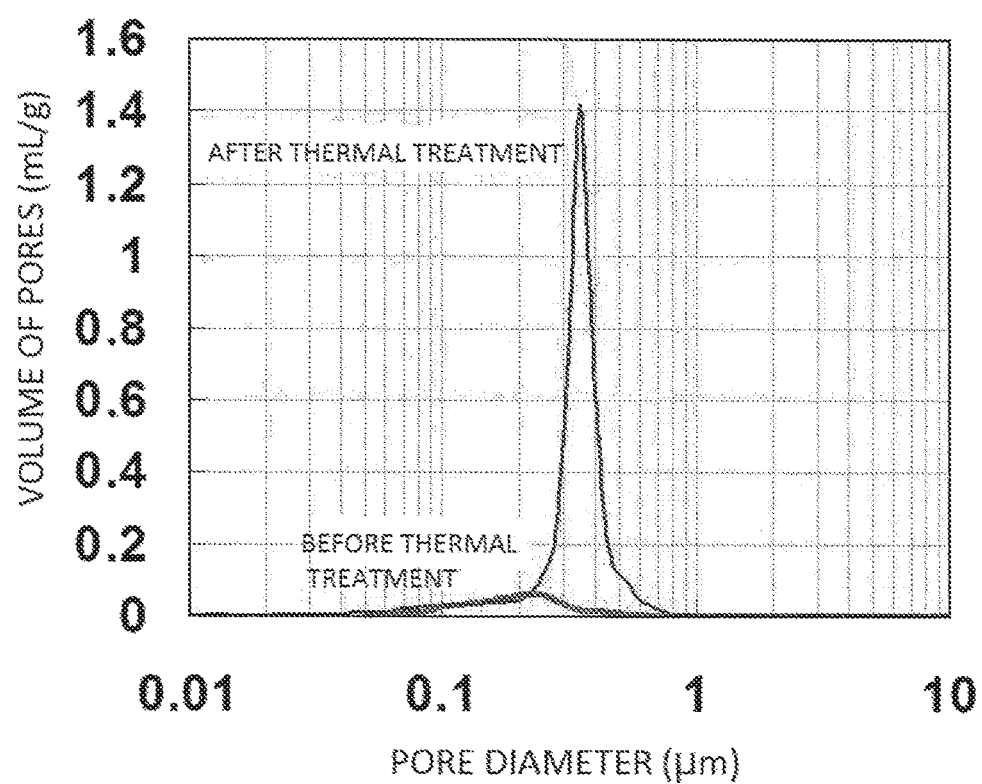

FORMED BODY AND METHOD FOR PRODUCING THE SAME, α-OLEFIN DIMERIZATION CATALYST, AND METHOD FOR PRODUCING α-OLEFIN DIMER

TECHNICAL FIELD

The present invention relates to a formed body that is useful as a catalyst support and a method for producing the same, an α-olefin dimerization catalyst produced from the formed body, and a method for producing an α-olefin dimer using the catalyst.

BACKGROUND ART

Alpha-olefin dimers typified by 4-methyl-1-pentene (including codimers; the same applies hereinafter) are utilized as monomers for the production of polyolefins. Many basic catalysts have been conventionally proposed as catalysts for the production of corresponding dimers through α-olefin dimerization reactions (including codimerization reactions; the same applies hereinafter). Especially, many catalysts obtained by supporting an alkali metal on a support mainly containing an anhydrous potassium compound have been used.

On these catalysts, studies for further enhancing the activity and selectivity to target substances have been made continuously. Also, due to their insufficient catalyst lifetime despite high initial activity, studies for extending the catalyst lifetime have been also made continuously. For example, Japanese Patent Application Laid-Open (JP-A) Nos. S58-114737, H3-42043, H7-222927, 2006-326418, and 2008-149275, and U.S. Pat. No. 5,081,094 describe to adjust physical properties of anhydrous potassium compounds or supports to be used so that the improvements in activity, selectivity and catalyst lifetime are pursued.

SUMMARY OF INVENTION

Technical Problem

The present inventors made various reviews on catalysts typified by those disclosed in these patent documents. As a result, it was found that the catalysts disclosed in JP-A Nos. S58-114737, H3-42043, H7-222927, 2006-326418, and 2008-149275 exhibit somewhat good effects of improvements in their activity and selectivity, but have tendencies to exhibit collapse of the catalyst supports in long-term reactions, leading to difficulty in continuous operation.

In addition, the catalyst using a support containing potassium hydrogen carbonate, as disclosed in U.S. Pat. No. 5,081,094, was found that it is powdery and thus unsuitable for industrial production. U.S. Pat. No. 5,081,094 discloses that the support may be formed into pellets and the like, but it is inferred that the use of water in forming causes dissolution of potassium hydrogen carbonate therein, resulting in failure to smoothly fill the support in a forming die and unhomogeneous physical properties of formed bodies.

Hence, an object of the invention is to provide a high-strength and porous formed body for use in supports for α-olefin dimerization catalysts, which is difficult to collapse during α-olefin dimerization reactions, can stably maintain the reactions over a long term, has high reaction activity and reaction selectivity, and a method for producing the formed body. A further object of the invention is to provide an α-olefin dimerization catalyst using the formed body, and a method for producing α-olefin dimer using the catalyst.

Solution to Problem

As a result of repeated reviews to attain the objects described above, the present inventors have found that the above objects can be attained by using, as a catalyst support, a formed body containing at least one of sodium carbonate or potassium carbonate and having specific volume of pores and crushing strength. Also, the present inventors have found that the above-specified formed body is obtained by incorporating a hydrogen carbonate compound into a raw material for a formed body to be used as a catalyst support, forming this raw material, and thermally treating the formed material at a specific temperature, whereby the above objects can be attained. The present inventors have, at last, completed the invention.

The means for attaining the above objects are as follows.
[1] A formed body, containing at least one carbonate compound (A1) selected from $Na_2CO_3$ or $K_2CO_3$, the formed body having a volume of pores with a pore diameter of from 0.05 μm to 10 μm of from 0.10 mL/g to 0.30 mL/g and a crushing strength of from 1.8 kgf to 10.0 kgf.
[2] The formed body according to the above [1], wherein a content ratio of the carbonate compound (A1) is 70% by mass or more.
[3] The formed body according to the above [1] or [2], further containing at least one compound (B1) represented by $Na_nY$ or $K_nY$, wherein Y is $SO_4$, $SiO_3$, F, Cl or Br, and n is an integer of 1 or 2 determined by the valence of Y.
[4] The formed body according to any one of the above [1] to [3], wherein the volume of pores is from 0.14 mL/g to 0.28 mL/g, and the crushing strength is from 2.2 kgf to 8.5 kgf.
[5] The formed body according to any one of the above [1] to [4], wherein the carbonate compound (A1) is $K_2CO_3$.
[6] The formed body according to any one of the above [1] to [5], further containing graphite (C).
[7] An α-olefin dimerization catalyst obtained by supporting an alkali metal (D) on the formed body according to any one of the above [1] to [6].
[8] A method for producing an α-olefin dimer, the method containing performing an α-olefin dimerization reaction in the presence of the α-olefin dimerization catalyst according to the above [7].
[9] A method for producing the formed body according to the above [1], the method containing:
 forming a mixture of 100 parts by mass of a total amount of (A) and (B), the mixture comprising from 10 parts by mass to 100 parts by mass of at least one hydrogen carbonate compound (A) represented by $AHCO_3$, wherein A is Na or K, and 0 parts by mass to 90 parts by mass of at least one compound (B) represented by $B_nX$, wherein B is Na or K, X is $CO_3$, $SO_4$, $SiO_3$, F, Cl, or Br, and n is an integer of 1 or 2 determined by the valence of X; and
 thermally treating the resultant formed mixture at a temperature of from 100° C. to 500° C. to thermally decompose 97% by mass or more of the hydrogen carbonate compound (A).
[10] The method for producing the formed body according to the above [9], wherein the mixture is free of water.
[11] The method for producing the formed body according to the above [9] or [10], wherein the forming of the mixture is performed by tablet compression.

[12] The method for producing the formed body according to any one of the above [9] to [11], wherein the mixture has a median diameter (d50), at a volume statistic, of from 5 μm to 600 μm.

[13] The method for producing the formed body according to any one of the above [9] to [12], wherein a content ratio of particles with a particle diameter of 40 μm or less is from 3% by mass to 30% by mass in the mixture.

Advantageous Effects of Invention

The formed body of the invention has high strength and is porous. An α-olefin dimerization catalyst, in which the formed body is used as a support of the α-olefin dimerization catalyst has higher reaction activity and reaction selectivity than those of known catalysts, and, further, is difficult to collapse in a reaction and can exhibit a remarkably improved catalyst lifetime.

BRIEF DESCRIPTION OF DRAWINGS

FIG. 1 shows measurement results of the pore distribution of formed bodies before and after thermal treatment in Example 1.

DESCRIPTION OF EMBODIMENTS

Hereinafter, a formed body and a method for producing the formed body, an α-olefin dimerization catalyst produced from the formed body, and a method for producing an α-olefin dimer using the catalyst, according to the present invention will be explained.

In this specification, numerical ranges depicted with "from" and "to" represent ranges inclusive of the numbers that respectively appear at the left and right of "to" as the minimum value and the maximum value, respectively.

The unit [kgf] of crushing strength as used herein can be converted into [N] based on the relational expression: 1 kgf=9.8 N.

<Formed Body>

The formed body of the invention contains at least one carbonate compound (A1) selected from $Na_2CO_3$ or $K_2CO_3$, the formed body has a volume of pores with a pore diameter of from 0.05 μm to 10 μm of from 0.10 mL/g to 0.30 mL/g and a crushing strength of from 1.8 kgf to 10.0 kgf.

When the volume of pores is 0.10 mL/g or more, the amount of the alkali metal supported on the formed body can be increased, and when the volume of pores is 0.30 mL/g or less, the strength of the formed body can be enhanced.

When the crushing strength is 1.8 kgf or more, the catalyst lifetime can be improved, and when the crushing strength is 10.0 kgf or less, the reduction in pore volume can be prevented.

The volume of pores with a pore diameter lying within the above range can generally be measured using a mercury porosimeter by the mercury intrusion method. The volume of pores is preferably from 0.14 mL/g to 0.28 mL/g, and more preferably from 0.15 mL/g to 0.25 mL/g. The volume of pores can be adjusted by adjusting the proportion of the hydrogen carbonate compound (A) to be incorporated in the mixture which serves as the raw material for the formed body. Also, the volume of pores can be adjusted by adjusting the density of the tablet compressed body which will be described later.

The crushing strength as used herein refers to the strength of the formed body in the radial direction. A direction corresponding to the radial direction is present in all of noodle shape, columnar shape, convex shape, ring shape and spherical shape which will be described later. In the case of formed bodies which are in shapes having no direction corresponding to the radial direction, the strength in the weakest direction is defined as the crushing strength. The crushing strength is generally known as a physical property which represents the pressure resistance strength of granules, and determined by pressurizing one pellet, tablet or other formed body in the barrel direction and measuring the force when the formed body is crushed. JIS Z8841 "Granules and agglomerates-Test method for strength" prescribes a method for testing the strength.

The crushing strength is preferably from 1.8 kgf to 8.5 kgf, more preferably from 2.2 kgf to 8.5 kgf, further preferably from 4.6 kgf to 8.4 kgf.

The formed body of the invention may further contain at least one compound (B1) represented by $Na_nY$ or $K_nY$, wherein Y is $SO_4$, $SiO_3$, F, Cl or Br, and n is an integer of 1 or 2 determined by the valence of Y.

The formed body of the invention may further contain graphite (C).

Hereinafter, each of the components of the formed body will be explained.

[At Least One Carbonate Compound (A1) Selected from $Na_2CO_3$ or $K_2CO_3$]

The carbonate compound (A1) is selected from sodium carbonate ($Na_2CO_3$) and potassium carbonate ($K_2CO_3$), and may contain either one or two of them. When the carbonate compound (A1) contains two of them, the mixing ratio thereof is not particularly limited. The carbonate compound (A1) is preferably $K_2CO_3$. The content ratio of the carbonate compound (A1) is preferably 70% by mass or more, more preferably 80% by mass or more, and further preferably 90% by mass or more.

[At Least One Compound (B1) Represented by $Na_nY$ or $K_nY$]

In the formula represented by $Na_nY$ or $K_nY$, Y is $SO_4$, $SiO_3$, F, Cl or Br and n is an integer of 1 or 2 determined by the valence of Y. Specifically, the compound (B1) is a sulfate, sulfite, fluoride, chloride or bromide of sodium or potassium. The compound (B1) may be either one compound represented by $Na_nY$ or $K_nY$, or contain two or more of them. When the compound (B1) contains two or more of them, the mixing ratio thereof is not particularly limited.

When the compound (B1) is contained in the formed body, the content ratio thereof is preferably more than 0% by mass and 30% by mass or less, more preferably more than 0% by mass and 20% by mass or less, and further preferably more than 0% by mass and 10% by mass or less.

[Graphite (C)]

The graphite (C) that may be contained in the formed body corresponds to graphite (C) which will be described in the section "Forming of Mixture" later. While the graphite (C) added to the raw material mixture for the formed body can be oxidized depending on the thermal treatment temperature and atmosphere, an optional amount of the graphite (C) added to the raw material may remain in the formed body.

When the graphite (C) is contained in the formed body, the content ratio thereof is preferably more than 0%/by mass and 10% by mass or less, and more preferably more than 0% by mass and 5% by mass or less.

<Method for Producing Formed Body>

The method for producing the formed body of the invention includes forming a mixture (100 parts by mass of the total of (A) and (B)) containing from 10 parts by mass to 100 parts by mass of at least one hydrogen carbonate compound (A) represented by $AHCO_3$, and 0 parts by mass to 90 parts by mass of at least one compound (B) represented by $B_nX$, and thermally treating the resultant formed mixture at a temperature of from 100 CC to 500° C. to thermally decompose 97% by mass or more of the hydrogen carbonate compound (A).

Hereinafter, the raw material for the formed body and conditions for producing the formed body will be explained in detail.

[At Least One Carbonate Compound (A) Represented by $AHCO_3$]

In the formula represented by $AHCO_3$, A is Na or K. Specifically, the hydrogen carbonate compound (A) is at least one compound selected from sodium hydrogen carbonate or potassium hydrogen carbonate. The hydrogen carbonate compound (A) may be one compound represented by $AHCO_3$, or contain two or more of them. When the hydrogen carbonate compound (A) contains two or more of them, the mixing ratio thereof is not particularly limited.

The production method of the invention essentially requires a thermal treatment step as will be described later. The hydrogen carbonate compound (A) is characterized by being a compound to be thermally decomposed in the step.

Among the above hydrogen carbonate compounds, potassium hydrogen carbonate of the formula wherein A is K is especially preferably used.

[At Least One Compound (B) Represented by $B_nX$]

In the formula represented by $B_nX$, B is Na or K, X is $CO_3$, $SO_4$, $SiO_3$, F, Cl, or Br, and n is an integer of 1 or 2 determined by the valence of X. Specifically, the compound (B) is a carbonate, sulfate, sulfite, fluoride, chloride or bromide of sodium or potassium. The compound (B) may be either one of the compound represented by $B_nX$, or contain two or more of them. When the compound (B) contains two or more of them, the mixing ratio thereof is not particularly limited.

Among the above compounds, potassium carbonate of the formula wherein B is K, X is $CO_3$, and n is 2 is especially preferably used.

[Mixture]

The mixture which serves as a raw material for the formed body of the invention contains the above hydrogen carbonate compound (A) and the above compound (B). The content of the hydrogen carbonate compound (A) is from 10 parts by mass to 100 parts by mass, preferably from 30 parts by mass to 100 parts by mass, and more preferably from 40 parts by mass to 100 parts by mass, based on 100 parts by mass of the total content of the hydrogen carbonate compound (A) and the compound (B). The content of the compound (B) is from 0 parts by mass to 90 parts by mass, preferably from 0 parts by mass to 70 parts by mass, and more preferably from 0 parts by mass to 60 parts by mass, based on 100 parts by mass of the total content of the hydrogen carbonate compound (A) and the compound (B).

In the invention, the compound (B) encompasses the case where the content thereof is 0 parts by mass, i.e., no compound (B) is contained in the mixture. The reason for this is because, as described above, the thermal decomposition of the hydrogen carbonate compound (A) through the thermal treatment step leads to the presence of a compound corresponding to the carbonate compound (A1) in the formed body, and the compound would be suitably used as a support for the α-olefin dimerization catalyst as will be described later.

The content of the compound represented by $B_nX$ wherein X is $SO_4$, $SiO_3$, F, Cl, or Br is preferably 30 parts by mass or less, more preferably 20 parts by mass or less, and further preferably 10 parts by mass or less, based on 100 parts by mass of the total content of the hydrogen carbonate compound (A) and the compound (B).

The mixture which serves as a raw material for the formed body of the invention may contain compounds other than the above hydrogen carbonate compound (A) and the above compound (B) as long as the obtained formed body has the volume of pores of from 0.10 mL/g to 0.30 mL/g and the crushing strength of from 1.8 kgf to 10.0 kgf. Examples of such other compounds include ammonium hydrogen carbonate. A mixture containing ammonium hydrogen carbonate can provide an increased pore volume of the formed body.

In the production method of the invention, it is particularly preferable to use a mixture in which 10 parts by mass to 100 parts by mass of potassium hydrogen carbonate and 0 parts by mass to 90 parts by mass of potassium carbonate are mixed to attain 100 parts by mass of the total content of them.

[Characteristics of Mixture]

The mixture containing the above hydrogen carbonate compound (A) and the above compound (B) has a median diameter (d50), at a volume statistic, of preferably from 5 μm to 600 μm, more preferably from 20 μm to 500 μm, further preferably from 50 μm to 450 μm, and especially preferably from 50 μm to 300 μm.

The powder having a median diameter within the above range enables stable production of a formed body by virtue of its good flowability.

The content ratio of particles with a particle diameter of 40 μm or less is preferably from 3% by mass to 30% by mass in the mixture containing the above hydrogen carbonate compound (A) and the above compound (B).

Generally, small-size particles are known to be desirably excluded because of their bad movement during tablet compressing. However, when the content ratio of particles with a particle diameter of 40 μm or less is within the above range, higher formed body strength can be attained. In addition, when the content ratio of particles with a particle diameter of 40 μm or less is within the above range, the flowability of the formed body raw material can be ensured, and the blocking, for example, by clogging on the way during forming of the mixture, is less likely occurred, so that homogeneous filling of the mixture can be achieved. A difference in particle size distribution between the hydrogen carbonate compound (A) and the compound (B) is acceptable as long as the content ratio of particles with a particle diameter of 40 μm or less, as a whole, is within the above range after mixing of them.

[Forming of Mixture]

In the invention, the method for forming the mixture is not particularly limited, and methods such as extrusion forming, compression forming and granulation forming are employed. Since the above hydrogen carbonate compound (A) is dissolved in water, addition of no water in the mixture (i.e., the mixture is free of water) is preferred.

In the case of extrusion forming, a forming raw material with enough viscosity to maintain its shape given by addition of a liquid to the above mixture is passed into a die to be formed. Since the above hydrogen carbonate compound (A) is dissolved in water, a solvent in which the hydrogen carbonate compound (A) would not be dissolved (for example, organic solvent) is preferably used in extrusion forming.

In the case of compression forming, the mixture is typically filled in a mortar which serves as a die, and compressed with a pounder for forming.

The forming method in the invention is preferably compression forming, and especially preferably tablet compressing, in view of the nature of the mixture which serves as the raw material for the formed body. In the case of tablet compression, a raw material which satisfies the characteristics of the mixture as described above is homogeneously filled in a mortar, resulting in tendencies to attain a formed body with small variation in density.

In the case of tablet compressing, graphite (C) can be added, according to need, to the mixture containing the hydrogen carbonate compound (A) and the compound (B), for smooth movement of the mortar and the pounder. The nature of the graphite (C) is not particularly limited, and any graphite that is generally used as a lubricant during tableting may be used. Generally-used graphite has a median diameter (d50), at a volume statistic, is within the range of from 5 µm to 500 µm and a specific surface area, as measured by the BET method, is within the broad range of from 0.1 $m^2/g$ to 300 $m^2/g$. Graphite (C) may be either natural graphite or artificial graphite.

The addition amount of the graphite (C) to the mixture which serves as the raw material of the formed body can be optionally determined within a range which enables tablet compression, and is preferably from 0.3 parts by mass to 10 parts by mass, more preferably from 0.5 parts by mass to 5 parts by mass, based on 100 parts by mass of the mixture. When the addition amount of the graphite is within this range, problems such as a disadvantageous reduction in strength of the formed body due to an excessive addition amount are unlikely to occur, and, further, problems such as an unstable density of the formed body caused by increased friction between the mortar and the pounder due to an insufficient addition amount and unfavorable operation of the device, are unlikely to occur. Accordingly, the mixture can be well formed.

The density of the tablet compressed formed body is preferably from 1.6 g/mL to 2.3 g/mL, and more preferably from 1.8 g/mL to 2.2 g/mL. The density of the tablet compressed formed body can be adjusted by controlling the compression strength.

The size and shape of the formed body are not particularly limited. The shape of the formed body is variously selected depending on the conditions of the forming device and the like, and can take any of a noodle shape, columnar shape, convex shape, ring shape or spherical shape. In the case of tablet compressing, a columnar shape, convex shape and ring shape are preferred, and a columnar shape is more preferred from the viewpoints of easiness to form and strength. Commercial tablet compressing machines can be used, and may be either a rotary type or a press type. A device with an optimum scale can appropriately be selected depending on the amount of production. In the case of a columnar formed body, the mixture is typically formed into a diameter of from 2 mm to 5 mm and a height of from 2 mm to 6 mm. When the size of the formed body is within these ranges, a problem whereby an insufficient size of the formed body causes an increase in the number of times of tableting, leading to a reduction in productivity and an increase in costs, is less likely to occur. In addition, in a case in which the formed body is used as a catalyst support, a problem whereby an insufficient size of the formed body causes slow diffusion of the raw material and product within the reaction system, resulting in reduced reaction activity and selectivity, is less likely to occur.

[Thermal Treatment Step]

The formed body obtained by the above forming method undergoes a thermal treatment step, and, eventually, becomes the formed body of the invention.

The temperature in the thermal treatment step is within the range of from 100° C. to 500° C., preferably from 150° C. to 450° C., and more preferably from 180° C. to 400° C. The temperature can be optionally determined depending on the kind of the hydrogen carbonate compound (A) used. The decomposition initiation temperatures of sodium hydrogen carbonate and potassium hydrogen carbonate corresponding to the hydrogen carbonate compound (A) are 270° C. and 100° C., respectively.

By thermal treatment, 97% by mass or more, preferably 98% by mass or more, and more preferably 99% by mass or more of the hydrogen carbonate compound (A) is thermally decomposed.

The thermal decomposition rate is adjusted by the temperature and thermal treatment time employed in the thermal treatment step. In the case that the thermal treatment temperature is relatively low, the above heat decomposition rate can be achieved by elongating the thermal treatment time. When the thermal decomposition rate of the hydrogen carbonate compound (A) falls within the above range, a formed body with a sufficient pore volume which serves as a preferred support for α-olefin dimerization catalyst can be obtained.

When the formed body is thermally treated, the specification of a thermal treatment device is not particularly limited as long as it is designed to prevent the retention of the gas generated upon thermal decomposition therein. The thermal treatment device is preferably designed to enable compulsory discharge of the gas generated upon thermal decomposition. Examples of the method for compulsorily discharging the gas generated include introduction of air, reducing gas or inert gas. Among these methods, the use of air is especially desired from the viewpoint of operation. Also, the structure of the thermal treatment device is not particularly limited, and any common heating furnace, electric furnace, belt furnace, hot air circulating furnace and the like can be used.

In the production method according to the invention, thermal treatment after forming of the raw material as described above causes thermal decomposition of the hydrogen carbonate compound (A) and formation of voids in a portion from which the gas produced has been removed. In the prior art, the compression strength during forming was weakened to enable spaces to be formed among the particles, thereby obtaining a porous formed body. However, in such a case, the strength of the formed body tended to be weakened. On the other hand, the invention adopts a technique of thermally decomposing the hydrogen carbonate compound (A) which is present internally after forming of the formed body, thereby obtaining a porous formed body, and thus does not need to involve forming that sacrifices strength as in the prior art. In the production method of the invention, forming is performed while the compression strength is optimized to obtain high strength, and many pores can be formed thereafter. Therefore, it is possible to form a high-strength, porous formed body. The formed body obtained by such a method surprisingly shows hardly any reduction in strength in comparison with the formed body before the thermal treatment step, despite the presence of many pores inside the formed body, and has a larger volume of pores and higher strength than the formed bodies produced in accordance with the prior art.

In view of the above, the formed body produced by the production method of the invention is excellent in strength and shape homogeneity, and thus is suitable as a catalyst support, especially, a support for an α-olefin dimerization catalyst.

<α-Olefin Dimerization Catalyst>

The α-olefin dimerization catalyst of the invention is obtained by supporting an alkali metal (D) on the formed body of the invention.

Examples of the alkali metal (D) include sodium, potassium or a mixture of sodium and potassium. The alkali metal (D) is a non-ionized, zero-valent metal, and may contain a component other than the alkali metal as long as it has an alkali metal purity of 90% or more. Examples of the component other than the alkali metal include elements of Group I in the periodic table such as lithium and potassium, various oxides or hydroxides, and metal elements other than the elements of the Group I in the periodic table.

Various methods can be employed as the method for supporting the alkali metal (D) on a support which is formed from the formed body of the invention. The temperature during supporting treatment is usually from 150° C. to 400° C. From the viewpoint of obtaining a catalyst which is excellent in catalyst activity, catalyst lifetime and selectivity to α-olefin dimerization products, the temperature during the supporting treatment is preferably from 200° C. to 350° C., and is more preferably from 200° C. to 300° C. The atmosphere during the supporting treatment may be either a reducing atmosphere or an inert atmosphere as long as it is not a water atmosphere or an oxidizing atmosphere. In consideration of safety and economy, treatment is preferably performed in a nitrogen atmosphere.

During supporting treatment, the support is preferably vibrated, rotated or stirred in order to homogeneously support the alkali metal (D). The supported alkali metal (D)) is known to be brought in contact with the support under heating to cause an exchange reaction with the alkali metal in the support.

The content ratio (supporting ratio) of the alkali metal (D) in the α-olefin dimerization catalyst is usually from 0.5% by mass to 10% by mass, and is preferably from 1% by mass to 6% by mass when the total amount of the alkali metal (D) and the support is defined as 100% by mass.

The formed body of the invention is characterized by having higher formed body strength and a larger volume of pores than those of the formed body produced in accordance with the prior art. Due to such a large volume of pores, a larger amount of the alkali metal (D) can be supported. Since there is a correlation between the support rate of the alkali metal (D) and the catalyst activity, the α-olefin dimerization catalyst of the invention can perform a reaction with higher activity. In general, there is a tendency that higher activity causes increase in the load on the support, thereby increasing the possibility that the collapse of the catalyst support would proceed. However, the formed body of the invention has very high strength and is hard to cause such a problem, and thus is especially preferred.

<Method for Producing α-olefin Dimer>

The method for producing the α-olefin dimer of the invention involves a dimerization reaction of an α-olefin in the presence of the α-olefin dimerization catalyst of the invention.

Examples of the α-olefin include lower α-olefins such as ethylene, propylene, 1-butene, isobutylene and 1-pentene. Among these dimerization reactions, the α-olefin dimerization catalyst of the invention is preferably used in the production of 4-methyl-1-pentene through dimerization of propylene and production of 3-methyl-1-pentene through codimerization with 1-butene and ethylene.

The reaction temperature in the dimerization reaction of an α-olefin using the α-olefin dimerization catalyst of the invention is usually from 0° C. to 300° C., and is preferably from 50° C. to 200° C. The reaction pressure is usually from normal pressure to 19.6 MPa (200 kg/cm$^2$-G), and is preferably from 1.96 MPa to 14.7 MPa (from 20 kg/cm$^2$-G to 150 kg/cm$^2$-G).

The state of the α-olefin within a reactor varies depending on the reaction conditions and the kind of the α-olefin, but can, in general, take a liquid phase state, a gas phase state or a supercritical state. Among these states, the reaction is preferably performed in the gas phase or supercritical state. Also, the reaction can be performed either in a fixed bed system or in a fluidized bed system, but is preferably performed in a fixed bed system. When the reaction is performed in a fixed bed system, the liquid hourly space velocity (LHSV) of the α-olefin is usually from 0.1 hr$^{-1}$ to 10 hr$^{-1}$, and is preferably from 0.5 hr$^{-1}$ to 5 hr$^{-1}$. Unreacted α-olefins and product are separated from the mixture after completion of the reaction in accordance with a conventional method, and the unreacted α-olefins are circulated and recycled for reactions.

EXAMPLES

Hereinafter, the present invention will be described in detail by way of Examples, but is not limited to these Examples.

[Measurement of Median Diameter (d50)]

Thirty (30) g of a powder was put in the upper part of a mesh sieve with a size of from 20 μm to 850 μm in a glove box through which nitrogen was circulated, and sieved manually. The masses of the powders on the respective sieves after sieving were measured to calculate the median diameter (d50).

[Measurement of Content Ratio of Particles with Particle Diameter of 40 μm or Less]

Thirty (30) g of a powder was put in the upper part of a mesh sieve with a size of 40 μm in a glove box through which nitrogen was circulated, and sieved manually. The mass of the powder which had passed through the sieve was measured, and divided by 30 g put first to calculate the content ratio of the particles having a particle diameter of 40 μm or less.

[Measurement of Thermal Decomposition Rate of Hydrogen Carbonate Compound (A)]

The temperature of the formed body obtained was increased up to 400° C. on a differential thermo-gravimetric analyzer (8120; manufactured by Rigaku Corporation), and thereafter the amount of the weight reduced was measured. From the relation between the content ratio of the hydrogen carbonate compound (A) during forming and the amount of the weight reduced, the thermal decomposition rate was calculated. Stoichiometrically, 1 mol of water and 1 mol of $CO_2$ are generated from 2 mol of the hydrogen carbonate compound (A). When the thermal decomposition rate is 100% by mass, no more thermal decomposition takes place, no reduction in weight on the differential thermo-gravimetric analyzer would be observed.

[Measurement of Volume of Pores]

The volume of pores having a pore diameter of from 0.05 μm to 10 μm was measured using a mercury porosimeter (Auto Pore IV; manufactured by MicroMetrics Japan) by the mercury intrusion method.

[Measurement of Crushing Strength of Formed Body]

The crushing strength in the radial direction of the formed body (in barrel direction of the columnar formed body) was measured using a digital hardness meter (KHT-40N; manufactured by Fujiwara Scientific Company Co., Ltd.) in accordance with the method prescribed in JIS Z8841 "Granules and agglomerates-Test method for strength" With respect to Example 8, the crushing strength in the vertical direction of the formed body (axial direction of the columnar formed body) was also measured.

The principle of measurement of the crushing strength involves putting a columnar formed body to be measured on a sample table at rest, lowering a movable pressurizing surface from the upper part at a constant rate, and pushing the surface onto the columnar formed body to measure the strength when the surface crushes the formed body.

[Confirmation of Presence or Absence of Catalyst Powdering]

After termination of the dimerization reaction of an α-olefin (propylene), the α-olefin dimerization catalyst was taken out from the reactor to visually confirm the presence or absence of powdering of the catalyst.

Example 1

[Production of Formed Body]

Seventy (70) parts by mass of $KHCO_3$ (manufactured by JUNSEI CHEMICAL CO., LTD.; purity: 99% and Catalog No. 43300-1201), which is the hydrogen carbonate compound (A) and 30 parts by mass of $K_2CO_3$ (purity: 99%; specific surface area measured by the BET method: 1.3 m$^2$/g; and bulk density: 0.46 g/mL), which is the compound (B), were mixed, thereby yielding 100 parts by mass of a powder mixture. The median diameter (d50) of the powder mixture was 120 μm, and the content ratio of the particles having a particle diameter of 40 μm or less was 7.5% by mass.

Into 100 parts by mass of the powder mixture, 0.9 parts by mass of graphite (purity: 98%; median diameter (d50): 0.6 μm; and specific surface area measured by the BET method: 150 m$^2$/g) was mixed homogeneously, and the resultant mixture was used as a tablet compressing raw material and was tablet compressed while the compression strength was controlled so as to attain a density of the tablet compressed formed body of 2.0 g/mL, thereby yielding a columnar tablet formed body having a diameter of 3 mm and a height of 3 mm. The tablet formed body had a volume of pores of 0.03 mL/g and a crushing strength in the radial direction of 5.7 kgf. The resultant tablet compressed formed body was thermally treated at 300° C. for 2 hours in dry air, thereby yielding a thermally treated formed body (formed body (1)). The thermal decomposition rate of $KHCO_3$ was 100% by mass. The resultant thermally treated formed body had a volume of pores of 0.21 mL/g and a crushing strength in the radial direction of 7.0 kgf. FIG. 1 shows measurement results of the pore distribution of the thermally treated formed body (formed body (1)) and the formed body before thermal treatment at the time of measuring the volume of pores.

[Preparation of α-Olefin Dimerization Catalyst]

Ninety six point five (96.5) parts by mass of the formed body (1) was dried at 300° C. for 2 hours in a nitrogen gas stream, and then 3.5 parts by mass of sodium was added thereto in a nitrogen atmosphere gas stream. The mixture was stirred at 280° C. for 3.5 hours to prepare an α-olefin dimerization catalyst (1).

Since residue of the added sodium remaining in a container was not observed, it was judged that all the amount of sodium was supported on the formed body. The supporting ratio at this time was 3.5% by mass.

[Dimerization Reaction of Propylene]

Four (4) grams of the α-olefin dimerization catalyst (1) obtained by the preparation method was placed in a tubular reactor (diameter: 18 mm), and propylene was continuously fed to a catalyst layer at a reactor internal temperature of 140° C., a reaction pressure of 9.8 MPa, a propylene flow rate of 4 g/h to perform a synthesis reaction of 4-methyl-1-pentene (hereinafter abbreviated as 4MP-1) through the dimerization reaction of propylene. Table 1 indicates the propylene conversion and 4MP-1 selectivity when the flow reaction was performed for 180 hours.

Example 2

[Preparation of α-Olefin Dimerization Catalyst]

Ninety four (94) parts by mass of the formed body (1) obtained in Example 1 was dried at 300° C. for 2 hours in a nitrogen gas stream, and then 6 parts by mass of sodium was added thereto in a nitrogen atmosphere gas stream. The mixture was stirred at 280° C. for 3.5 hours to prepare an α-olefin dimerization catalyst (2).

Since residue of the added sodium remaining in a container was not observed, it was judged that all the amount of sodium was supported on the formed body. The supporting ratio at this time was 6.0% by mass.

[Dimerization Reaction of Propylene]

A synthesis reaction of 4MP-1 through the dimerization reaction of propylene was performed using 4 g of the α-olefin dimerization catalyst (2) obtained by the above preparation method by a method similar to that employed in Example 1. Table 1 indicates the propylene conversion and 4MP-1 selectivity when the flow reaction was performed for 180 hours.

Example 3

[Production of Formed Body]

$KHCO_3$ (manufactured by JUNSEI CHEMICAL CO., LTD.; purity: 99% or more and Catalog No. 43300-1201) was used as the hydrogen carbonate compound (A). $KHCO_3$ had a median diameter (d50) of 150 μm, and the content ratio of particles with a particle diameter of 40 μm or less was 3.0% by mass.

Into 100 parts by mass of $KHCO_3$, 0.9 parts by mass of graphite (purity: 98%; median diameter (d50): 0.6 μm; and specific surface area measured by the BET method: 150 m$^2$/g) was mixed homogeneously, and the resultant mixture was used as a tablet compressing raw material and was tablet compressed while the compression strength was controlled so as to attain a density of the tablet compressed formed body of 2.0 g/mL, thereby yielding a columnar tablet formed body having a diameter of 3 mm and a height of 3 mm. The resultant tablet compressed formed body was thermally treated at 300° C. for 2 hours in dry air, thereby yielding a thermally treated formed body (formed body (2)). The thermal decomposition rate of $KHCO_3$ was 100% by mass. The resultant thermally treated formed body had a volume of pores of 025 mL/g and a crushing strength in the radial direction of 6.0 kgf.

[Preparation of α-Olefin Dimerization Catalyst]

Ninety six point five (96.5) parts by mass of the formed body (2) was dried at 300° C. for 2 hours in a nitrogen gas stream, and then 3.5 parts by mass of sodium was added thereto in a nitrogen atmosphere gas stream. The mixture was stirred at 280° C. for 3.5 hours to prepare an α-olefin dimerization catalyst (3).

Since residue of the added sodium remaining in a container was not observed, it was judged that all the amount of sodium was supported on the formed body. The supporting ratio at this time was 3.5% by mass.

[Dimerization Reaction of Propylene]

A synthesis reaction of 4MP-1 through the dimerization reaction of propylene was performed using 4 g of the α-olefin dimerization catalyst (3) obtained by the above preparation method by a method similar to that employed in Example 1, Table 1 indicates the propylene conversion and 4MP-1 selectivity when the flow reaction was performed for 180 hours.

Example 4

[Production of Formed Body]

One hundred (100) parts by mass of a powder mixture was obtained in a similar manner as in Example 1 except that the amount of $KHCO_3$ to be used was defined as 50 parts by mass and that the amount of $K_2CO_3$ to be used was defined as 50 parts by mass. The powder mixture had a median diameter (d50) of 100 μm and a content ratio of particles with a particle diameter of 40 μm or less of 13.0% by mass.

A thermally treated formed body (formed body (3)) was obtained in a similar manner as in Example 1 except that 0.9 parts by mass of graphite (purity: 98%; median diameter (d50): 0.6 μm; and specific surface area measured by the BET method: 150 m$^2$/g) was homogeneously mixed into 100 parts by mass of the powder mixture, and that the resultant mixture was used as a tablet compressing raw material and was tablet compressed while the compression strength was controlled so as to attain a density of the tablet compressed formed body of 1.9 g/mL. The thermal decomposition rate of $KHCO_3$ was 100% by mass. The resultant thermally treated formed body had a volume of pores of 0.21 mL/g and a crushing strength in the radial direction of 4.6 kgf.

[Preparation of α-Olefin Dimerization Catalyst]

Ninety six point five (96.5) parts by mass of the formed body (3) was dried at 300° C. for 2 hours in a nitrogen gas stream, and then 3.5 parts by mass of sodium was added thereto in a nitrogen atmosphere gas stream. The mixture was stirred at 280° C. for 3.5 hours to prepare an α-olefin dimerization catalyst (4).

Since residue of the added sodium remaining in a container was not observed, it was judged that all the amount of sodium was supported on the formed body. The supporting ratio at this time was 3.5% by mass.

[Dimerization Reaction of Propylene]

A synthesis reaction of 4MP-1 through the dimerization reaction of propylene was performed using 4 g of the α-olefin dimerization catalyst (4) obtained by the above preparation method by a method similar to that employed in Example 1. Table 1 indicates the propylene conversion and 4MP-1 selectivity when the flow reaction was performed for 180 hours.

Example 5

[Production of Formed Body]

One hundred (100) parts by mass of a powder mixture was obtained in a similar manner as in Example 1 except that $K_2CO_3$ pulverized by lightly crushing in a mortar and then passed through a 212-μm sieve was used. The powder mixture had a median diameter (d50) of 100 μm and a content ratio of particles with a particle diameter of 40 μm or less of 23.0% by mass.

A thermally treated formed body (formed body (4)) was obtained in a similar manner as in Example 1 except that 0.9 parts by mass of graphite (purity: 98%; median diameter (d50): 0.6 μm; and specific surface area measured by the BET method: 150 m$^2$/g) was homogeneously mixed into 100 parts by mass of the powder mixture, the mixture was used as a tablet compressing raw material, and that the compression strength was controlled so as to attain a density of the tablet compressed formed body of 2.0 g/mL. The thermal decomposition rate of $KHCO_3$ was 100% by mass. The resultant thermally treated formed body had a volume of pores of 0.20 mL/g and a crushing strength in the radial direction of 8.4 kgf.

[Preparation of α-Olefin Dimerization Catalyst]

Ninety six point five (96.5) parts by mass of the formed body (4) was dried at 300° C. for 2 hours in a nitrogen gas stream, and then 3.5 parts by mass of sodium was added thereto in a nitrogen atmosphere gas stream. The mixture was stirred at 280° C. for 3.5 hours to prepare an α-olefin dimerization catalyst (5).

Since residue of the added sodium remaining in a container was not observed, it was judged that all the amount of sodium was supported on the formed body. The supporting ratio at this time was 3.5% by mass.

[Dimerization Reaction of Propylene]

A synthesis reaction of 4MP-1 through the dimerization reaction of propylene was performed using 4 g of the α-olefin dimerization catalyst (5) obtained by the above preparation method by a method similar to that employed in Example 1. Table 2 indicates the propylene conversion and 4MP-1 selectivity when the flow reaction was performed for 180 hours.

Example 6

[Production of Formed Body]

One hundred (100) parts by mass of a powder mixture was obtained in a similar manner as in Example 4 except that $K_2CO_3$ pulverized by lightly crushing in a mortar and then passed through a 212-μm sieve was used. The powder mixture had a median diameter (d50) of 90 μm and a content ratio of particles with a particle diameter of 40 μm or less of 26.5% by mass.

A thermally treated formed body (formed body (5)) was obtained in a similar manner as in Example 1 except that 0.9 parts by mass of graphite (purity: 98%; median diameter (d50): 0.6 μm; and specific surface area measured by the BET method: 150 m$^2$/g) was homogeneously mixed into 100 parts by mass of the powder mixture, the mixture was used as a tablet compressing raw material, and that the compression strength was controlled so as to attain a density of the tablet compressed formed body of 1.9 g/mL. The thermal decomposition rate of $KHCO_3$ was 100% by mass. The resultant thermally treated formed body had a volume of pores of 0.20 mL/g and a crushing strength in the radial direction of 7.8 kgf.

[Preparation Method of α-Olefin Dimerization Catalyst]

Ninety six point five (96.5) parts by mass of the formed body (5) was dried at 300° C. for 2 hours in a nitrogen gas stream, and then 3.5 parts by mass of sodium was added thereto in a nitrogen atmosphere gas stream. The mixture was stirred at 280° C. for 3.5 hours to prepare an α-olefin dimerization catalyst (6).

Since residue of the added sodium remaining in a container was not observed, it was judged that all the amount of sodium was supported on the formed body. The supporting ratio at this time was 3.5% by mass.

[Dimerization Reaction of Propylene]

A synthesis reaction of 4MP-1 through the dimerization reaction of propylene was performed using 4 g of the α-olefin dimerization catalyst (6) obtained by the above preparation method by a method similar to that employed in Example 1. Table 2 indicates the propylene conversion and 4MP-1 selectivity when the flow reaction was performed for 180 hours.

Example 7

[Production of Formed Body]

Thirteen (13) parts by mass of a powder (median diameter (d50): 15 μm) obtained by pulverizing $KHCO_3$ (manufactured by JUNSEI CHEMICAL CO., LTD.; purity: 99% and Catalog No. 43300-1201), which is the hydrogen carbonate compound (A), in a mortar and 87 parts by mass of $K_2CO_3$ (purity: 99%; specific surface area measured by the BET method: 1.2 m$^2$/g; and bulk density: 0.94 g/mL), which is the compound (B), were mixed, thereby yielding 100 parts by mass of a powder mixture. The powder mixture had a median diameter (d50) of 260 μm and a content ratio of particles with a particle diameter of 40 μm or less of 14.6% by mass.

Into 100 parts by mass of the powder mixture, 0.9 parts by mass of graphite (median diameter (d50): 0.6 μm; and specific surface area measured by the BET method: 150 m$^2$/g) was mixed homogeneously, and the resultant mixture was used as a tablet compressing raw material and was tablet compressed while the compression strength was controlled so as to attain a density of the tablet compressed formed body of 1.8 g/mL, thereby yielding a columnar tablet formed body having a diameter of 3 mm and a height of 3 mm. During the tablet compressing, the compression strength was stably maintained, and stable tablet compressing could be performed. The resultant tablet compressed formed body was thermally treated at 300° C. for 2 hours in dry air, thereby yielding a thermally treated formed body (formed body (6)). The thermal decomposition rate of $KHCO_3$ was 100% by mass. The resultant thermally treated formed body had a pore volume of 0.15 mL/g and a crushing strength in the radial direction of 5.9 kgf.

[Preparation of α-Olefin Dimerization Catalyst]

Ninety six point five (96.5) parts by mass of the formed body (6) was dried at 300° C. for 2 hours in a nitrogen gas stream, and then 3.5 parts by mass of sodium was added thereto in a nitrogen atmosphere gas stream. The mixture was stirred at 280° C. for 3.5 hours to prepare an α-olefin dimerization catalyst (7).

Since residue of the added sodium remaining in a container was not observed, it was judged that all the amount of sodium was supported on the formed body. The supporting ratio at this time was 3.5% by mass.

[Dimerization Reaction of Propylene]

A synthesis reaction of 4MP-1 through the dimerization reaction of propylene was performed by placing 4 g of the α-olefin dimerization catalyst (7) obtained by the above preparation method in a tubular reactor (diameter: 18 mm) and continuously feeding propylene to a catalyst layer at a reactor internal temperature of 140° C., a reaction pressure of 9.8 MPa and a propylene flow rate of 4 g/h. Table 2 indicates the propylene conversion and 4MP-1 selectivity when the flow reaction was performed for 180 hours.

Example 8

[Production of Formed Body]

One hundred (100) parts by mass of a powder mixture was obtained in a similar manner as in Example 1 except that the amount of $KHCO_3$ to be used was defined as 80 parts by mass and that the amount of $K_2CO_3$ to be used was defined as 20 parts by mass. The powder mixture had a median diameter (d50) of 120 μm and a content ratio of particles with a particle diameter of 40 μm or less of 5.0% by mass.

A thermally treated formed body (formed body (7)) was obtained in a similar manner as in Example 1 except that 0.9 parts by mass of graphite (purity: 98%; median diameter (d50): 0.6 μm; and specific surface area measured by the BET method: 150 m$^2$/g) was homogeneously mixed into 100 parts by mass of the powder mixture, the mixture was used as a tablet compressing raw material, and that the compression strength was controlled so as to attain a density of the tablet compressed formed body of 2.0 g/mL. The resultant thermally treated formed body had a volume of pores of 0.24 mL/g, a crushing strength in the radial direction of 5.2 kgf, and a crushing strength in the vertical direction of 22.5 kgf.

Comparative Example 1

[Production of Formed Body]

$K_2CO_3$ (manufactured by ASAHI GLASS CO., LTD.; purity: 99%) was used as the compound (B). $K_2CO_3$ had a median diameter (d50) of 110 μm, and the content ratio of particles with a particle diameter of 40 μm or less was 4.0% by mass.

Into 100 parts by mass of $K_2CO_3$, 0.9 parts by mass of graphite (median diameter (d50): 0.6 μm; and specific surface area measured by the BET method: 150 m$^2$/g) was mixed homogeneously, and the resultant mixture was used as a tablet compressing raw material and was tablet compressed while the compression strength was controlled so as to attain a density of the tablet compressed formed body of 2.0 g/mL, thereby yielding a columnar tablet formed body having a diameter of 3 mm and a height of 3 mm. The resultant tablet compressed formed body was thermally treated at 300° C. for 2 hours in dry air, thereby yielding a thermally treated formed body (formed body (C1)). The resultant thermally treated formed body had a volume of pores of 0.05 mL/g and a crushing strength in the radial direction of 6.0 kgf.

[Preparation of α-Olefin Dimerization Catalyst]

Ninety six point five (96.5) parts by mass of the formed body (C1) was dried at 300° C. for 2 hours in a nitrogen gas stream, and then 3.5 parts by mass of sodium was added thereto in a nitrogen atmosphere gas stream. The mixture was stirred at 280° C. for 3.5 hours to prepare an α-olefin dimerization catalyst (C1).

The added sodium was fixed to the inside of the container and the outer surface of the formed body, and some thereof was difficult to discharge from the container. Thus, it was judged that not all the amount of the added sodium was supported on the formed body. The supporting ratio at this time is considered to have been below 3.5% by mass.

Comparative Example 2

[Preparation Method of α-Olefin Dimerization Catalyst]

Ninety nine (99) parts by mass of the formed body (C1) obtained in Comparative Example 1 was dried at 300° C. for 2 hours in a nitrogen gas stream, and then 1 part by mass of sodium was added thereto in a nitrogen atmosphere gas stream. The mixture was stirred at 280° C. for 3.5 hours to prepare an α-olefin dimerization catalyst (C2).

Since residue of the added sodium remaining in a container was not observed, it was judged that all the amount of sodium was supported on the formed body. The supporting ratio at this time was 1.0% by mass.

[Dimerization Reaction of Propylene]

A synthesis reaction of 4MP-1 through the dimerization reaction of propylene was performed using 4 g of the α-olefin dimerization catalyst (C2) obtained by the above preparation method by a method similar to that employed in Example 1. Table 3 indicates the propylene conversion and 4MP-1 selectivity when the flow reaction was performed for 180 hours.

Comparative Example 3

[Production of Formed Body]

A thermally treated formed body (formed body (C2)) was obtained in a similar manner as in Comparative Example 1 except that tablet forming was performed while the compression strength was controlled so as to attain a density of the tablet compressed formed body of 1.55 g/mL. The resultant thermally treated formed body had a volume of pores of 0.21 mL/g and a crushing strength in the radial direction of 1.1 kgf.

[Preparation of α-Olefin Dimerization Catalyst]

Ninety six point five (96.5) parts by mass of the formed body (C2) was dried at 300° C. for 2 hours in a nitrogen gas stream, and then 3.5 parts by mass of sodium was added thereto in a nitrogen atmosphere gas stream. The mixture was stirred at 280° C. for 3.5 hours to attempt to prepare an α-olefin dimerization catalyst (C3). However, powderization of the formed body (C2) was occurred during supporting, and thus could not be recovered as a catalyst.

TABLE 1

| | | Example 1 | Example 2 | Example 3 | Example 4 |
|---|---|---|---|---|---|
| Tablet forming step | Formed body No. | (1) | | (2) | (3) |
| | (A) KHCO$_3$ (parts by mass) | 70 | | 100 | 50 |
| | (B) K$_2$CO$_3$ (parts by mass) | 30 | | 0 | 50 |
| | Total of (A) + (B) | 100 | | 100 | 100 |
| | Median diameter (μm) | 120 | | 150 | 100 |
| | Content ratio of particles with particle diameter of 40 μm or less (mass %) | 7.5 | | 3.0 | 13.0 |
| | Volume of pores (mL/g) | 0.21 | | 0.25 | 0.21 |
| | Crushing strength in radial direction (kgf) | 7.0 | | 6.0 | 4.6 |
| | Crushing strength in vertical direction (kgf) | — | | — | — |
| Sodium supporting step | α-olefin dimerization catalyst No. | (1) | (2) | (3) | (4) |
| | Supporting ratio (mass %) | 3.5 | 6.0 | 3.5 | 3.5 |
| | All amount of alkali supported | OK | OK | OK | OK |
| Dimerization reaction step*) | Propylene conversion (%) | 21.8 | 39.6 | 24.0 | 21.2 |
| | 4MP-1 selectivity (%) | 90.5 | 88.9 | 91.0 | 90.2 |
| | Presence or absence of catalyst powdering | Absent | Absent | Absent | Absent |

*)Reaction conditions: catalyst amount: 4 g; propylene flow rate: 4 g/h; 140° C.; 180 h

TABLE 2

| | | Example 5 | Example 6 | Example 7 | Example 8 |
|---|---|---|---|---|---|
| Tablet forming step | Formed body No. | (4) | (5) | (6) | (7) |
| | (A) KHCO$_3$ (parts by mass) | 70 | 50 | 13 | 80 |
| | (B) K$_2$CO$_3$ (parts by mass) | 30 | 50 | 87 | 20 |
| | Total of (A) + (B) | 100 | 100 | 100 | 100 |
| | Median diameter (μm) | 100 | 90 | 260 | 120 |
| | Content ratio of particles with particle diameter of 40 μm or less (mass %) | 23.0 | 26.5 | 14.6 | 5.0 |
| | Volume of pores (mL/g) | 0.20 | 0.20 | 0.15 | 0.24 |
| | Crushing strength in radial direction (kgf) | 8.4 | 7.8 | 5.9 | 5.2 |
| | Crushing strength in vertical direction (kgf) | — | — | — | 22.5 |
| Sodium supporting step | α-olefin dimerization catalyst No. | (5) | (6) | (7) | — |
| | Supporting ratio (mass %) | 3.5 | 3.5 | 3.5 | — |
| | All amount of alkali supported | OK | OK | OK | — |
| Dimerization reaction step*) | Propylene conversion (%) | 21.3 | 22.1 | 21.2 | — |
| | 4MP-1 selectivity (%) | 90.7 | 90.5 | 91.1 | — |
| | Presence or absence of catalyst powdering | Absent | Absent | Absent | — |

*)Reaction conditions: catalyst amount: 4 g; propylene flow rate: 4 g/h; 140° C.; 180 h

TABLE 3

|  |  | Comparative Example 1 | Comparative Example 2 | Comparative Example 3 |
|---|---|---|---|---|
| Tablet forming step | Formed body No. | (C1) | | (C2) |
| | (A) KHCO$_3$ (parts by mass) | | 0 | |
| | (B) K$_2$CO$_3$ (parts by mass) | | 100 | |
| | Total of (A) + (B) | | 100 | |
| | Median diameter (μm) | | 110 | |
| | Content ratio of particles witn particle diameter of 40 μm or less (mass %) | | 4.0 | |
| | Volume of pores (mL/g) | | 0.05 | 0.21 |
| | Crushing strength in radial direction (kgf) | | 6.0 | 1.1 |
| | Crushing strength in vertical direction (kgf) | — | — | — |
| Sodium supporting step | α-olefin dimerization catalyst No. | (C1) | (C2) | (C3) |
| | Supporting ratio (mass %) | (3.5)**) | 1.0 | 3.5 |
| | All amount of alkali supported | NG | OK | —***) |
| Dimerization reaction step*) | Propylene conversion (%) | — | 6.7 | — |
| | 4MP-1 selectivity (%) | — | 86.5 | — |
| | Presence or absence of catalyst powdering | — | Partly present | — |

*)Reaction conditions: catalyst amount: 4 g; propylene flow rate: 4 g/h; 140° C.; 180 h
**)Since not all the amount of the added sodium was supported on the formed body, it is inferred that the supporting rate would be lower than the numerical value.
***)The catalyst was powdered during supporting, and thus could not be recovered as a formed body.

Tables 1 to 3 indicate the physical properties of the formed bodies obtained in Examples 1 to 8 and Comparative Examples 1 to 3 and results of sodium supporting and propylene dimerization reaction. It can be seen that the invention provides a formed body having a large volume of pores and high crushing strength. High strength of the formed body can prevent the catalyst from being powdered in the subsequent alkali metal supporting step and α-olefin dimerization reaction step and enables preparation of a long-life catalyst. Also, due to a larger volume of pores of the formed body, all the amount of sodium is supported on the formed body even when the amount of sodium to be supported is increased. Accordingly, it can be understood that a catalyst having high reaction activity (herein, propylene conversion) is obtained.

The entire disclosure of Japanese Patent Application No. 2013-260226 filed on Dec. 17, 2013 is incorporated herein by reference.

All publications, patent applications, and technical standards described in the present specification are incorporated herein by reference to the same extent as if each publication, patent application, or technical standard was specifically and individually indicated to be incorporated by reference.

The invention claimed is:

1. An α-olefin dimerization catalyst comprising a formed body and an alkali metal (D) supported on the formed body, wherein the formed body comprises at least one carbonate compound (A1) selected from Na$_2$CO$_3$ or K$_2$CO$_3$ in a content of 70% by mass or more, the formed body having a volume of pores with a pore diameter of from 0.05 μm to 10 μm of from 0.10 mL/g to 0.30 mL/g and a crushing strength of from 1.8 kgf to 10.0 kgf.

2. A method for producing an α-olefin dimer, the method comprising performing an α-olefin dimerization reaction in the presence of the α-olefin dimerization catalyst according to claim 1.

3. A method for producing the α-olefin dimerization catalyst according to claim 1, the method comprising:
   forming a mixture of 100 parts by mass of a total amount of (A) and (B), the mixture comprising from 10 parts by mass to 100 parts by mass of at least one hydrogen carbonate compound (A) represented by AHCO$_3$, wherein A is Na or K, and 0 parts by mass to 90 parts by mass of at least one compound (B) represented by B$_n$X, wherein B is Na or K, X is CO$_3$, SO$_4$, SiO$_3$, F, Cl, or Br, and n is an integer of 1 or 2 determined by the valence of X, wherein a total amount of (A), and NaCO$_3$ and KCO$_3$ among (B) is 70 parts by mass or more; and
   thermally treating the resultant formed mixture at a temperature of from 100° C. to 500° C. to thermally decompose 97% by mass or more of the hydrogen carbonate compound (A) to form the formed body, and supporting the alkali metal (D) on the formed body.

4. The method according to claim 3, wherein the mixture is free of water.

5. The method according to claim 3, wherein the forming of the mixture is performed by tablet compression.

6. The method according to claim 3, wherein the mixture has a median diameter (d50), at a volume statistic, of from 5 μm to 600 μm.

7. The method according to claim 3, wherein a content ratio of particles with a particle diameter of 40 μm or less is from 3% by mass to 30% by mass in the mixture.

8. The α-olefin dimerization catalyst according to claim 1, further comprising at least one compound (B1) represented by Na$_n$Y or K$_n$Y, wherein Y is SO$_4$, SiO$_3$, F, Cl or Br, and n is an integer of 1 or 2 determined by the valence of Y.

9. The α-olefin dimerization catalyst according to claim 1, wherein the formed body is produced by a process comprising:
   forming a mixture of 100 parts by mass of a total amount of (A) and (B), the mixture comprising from 10 parts by mass to 100 parts by mass of at least one hydrogen carbonate compound (A) represented by AHCO$_3$, wherein A is Na or K, and 0 parts by mass to 90 parts by mass of at least one compound (B) represented by B$_n$X, wherein B is Na or K, X is CO$_3$, SO$_4$, SiO$_3$, F, Cl, or Br, and n is an integer of 1 or 2 determined by the valence of X, wherein a total amount of (A) and NaCO$_3$ and/or KCO$_3$ among (B) is 70 parts by mass or more; and
   thermally treating the resultant formed mixture at a temperature of from 100° C. to 500° C. to thermally decompose 97% by mass or more of the hydrogen carbonate compound (A).

10. The α-olefin dimerization catalyst according to claim 1, wherein the volume of pores is from 0.14 mL/g to 0.28 mL/g, and the crushing strength is from 2.2 kgf to 8.5 kgf.

11. The α-olefin dimerization catalyst according to claim 1, wherein the carbonate compound (A1) is $K_2CO_3$.

12. The α-olefin dimerization catalyst according to claim 1, further comprising graphite (C).

* * * * *